United States Patent [19]

Adams

[11] Patent Number: 4,602,638
[45] Date of Patent: Jul. 29, 1986

[54] APPARATUS AND METHOD FOR INVASIVE ELECTRICAL STIMULATION OF BONE FRACTURES

[76] Inventor: Eddie Adams, 2220 E. Franklin Ave., Minneapolis, Minn. 55404

[21] Appl. No.: 657,369

[22] Filed: Oct. 3, 1984

[51] Int. Cl.[4] ............................................. A61N 1/36
[52] U.S. Cl. ............................................. 128/419 F
[58] Field of Search ........ 128/419 P, 419 PG, 419 D, 128/419 F, 639–641, 643–644, 798–802

[56] References Cited

U.S. PATENT DOCUMENTS

| | | | |
|---|---|---|---|
| 3,244,174 | 4/1966 | Wesbey et al. | 128/419 P |
| 3,841,306 | 10/1974 | Hallgren | 128/419 F |
| 3,890,953 | 6/1975 | Kraus et al. | 128/419 F |
| 4,011,861 | 3/1977 | Enger | 128/642 |
| 4,030,509 | 6/1977 | Heilman et al. | 128/419 D |
| 4,105,017 | 8/1978 | Ryaby et al. | 128/419 F |
| 4,243,051 | 1/1981 | Wittemann | 128/802 |
| 4,300,567 | 11/1981 | Kolenik et al. | 128/419 D |
| 4,333,469 | 6/1982 | Jeffcoat et al. | 128/419 F |
| 4,524,087 | 6/1985 | Engel | 128/798 |

FOREIGN PATENT DOCUMENTS

| | | | |
|---|---|---|---|
| 83/02901 | 9/1983 | World Int. Prop. O. | 128/419 F |
| 766607 | 9/1980 | U.S.S.R. | 128/419 F |

Primary Examiner—William E. Kamm
Assistant Examiner—Mitchell J. Shein
Attorney, Agent, or Firm—Zarley, McKee, Thomte, Voorhees & Sease

[57] ABSTRACT

An invasive electrical stimulation device includes a cathode an anode, each comprising a thin electrically conductive sheet having one exposed surface and the opposite surface covered with an insulation layer. A pair of insulated leads connect the cathode and anode to an implantable power pac which includes a source of electric power and an insulating encasement surrounding the same. The cathode may be equipped with a plurality of spaced-apart FM channel monitors which are electrically connected to an FM telemetry component within the power pac for transmitting signals indicative of the healing response of a fracture to electrical stimulation. A frequency modulated current regulator may be added to the power pac for adjusting the amperage in response to FM control signals from a remote transmitter or automatically by an implantable computer assisted device.

11 Claims, 22 Drawing Figures

APPARATUS AND METHOD FOR INVASIVE ELECTRICAL STIMULATION OF BONE FRACTURES

BACKGROUND OF THE INVENTION

The present invention is directed generally to the electrical stimulation of both bone fractures and soft tissue to promote and expedite the healing thereof, and more particularly to a small thin invasive electrical stimulation device which can be easily implanted and which is operative to both monitor the healing process and to adjust the electrical stimulation in response thereto.

The general acceleration of bone fracture healing from electrical stimulation has been appreciated in the past, for example, in the analysis of Wolfian laws of soft tissue collagenous structures to fields. It is known that some specific functional link serves to transduce express electrical energies into a mechanical response, namely bone deposition, formation and cell differentiation. Cells respond and orientate to direct current field patterns under stimulation of cathode placement.

Certain minimum current is required to facilitate an initiating response to stimulus and to change the healing progression of bone and soft tissue. Optimal response amperage is approximately 20 microamps. Reduced amperage minimizes necrosis and increased amperage tends to maximize healing potential within finite variables.

Studies have shown electrical stimulation to effect nuclear and cytoplasmic RNA, pH of extra cellular environment which have been recorded to achieve optimal environments for manipulation of the osteoblastic response, increased DNA content, and organelle components of the cytoplasm, all of which reflect an advantageous facilitative response to healing.

The extracellular products of such cell types responding to electrical stimulation have been noted to respond in an organizational way to such fields, and might relate to extracellular-intracellular feedback mechanisms of control believed to be related to current density of stimulation and time sequence of need in healing fractures, which this invention addresses.

Osteogenesis has generally been performed by an only semiinvasive method. An example is the direct current bone growth stimulator marketed by Zimmer of Warsaw, Ind. 46580 and licensed under U.S. Pat. No. 3,842,841. In this system, several cathode needles are inserted through the skin into a bone fracture. An anode pad is externally situated adjacent the fracture and an external power source electrically connects the anode and cathode leads. Disadvantages of such known systems include the need for the patient to maintain the external device environment and the hazards of injury or accidental interruption in the patient's daily life routine. Whereas an implantable needle-like bone growth stimulator is disclosed in U.S. Pat. No. 4,333,469, no such device has previously been known which is sheet-like in construction and which is capable of progressively monitoring the healing response of a fracture to electrical stimulation and manipulating the current output of the apparatus for maximizing the potential healing response of bone and soft tissue repair.

Accordingly, a primary object of the invention is to provide an improved apparatus and method for the invasive electrical stimulation of bone fractures.

Another object is to provide an electrical stimulation device for bone fractures and soft tissue which is totally encapsulated and implantable so as to be much less cumbersome than externally supported devices and adaptable for healing more types of injuries.

Another object is to provide an apparatus and method of invasive electrical stimulation which include a novel cathode and anode designed for increased operative surface area.

Another object is to provide such an apparatus and method wherein the current density and timing of the output of the implanted power source can be externally monitored and adjusted.

Another object is to provide such an apparatus and method wherein the healing response of a fracture is monitorable at a plurality of positions and over a period of time.

Finally, an object is to provide a wholly invasive electrical stimulation device which is simple and rugged in construction, readily implantable, and efficient in operation.

SUMMARY OF THE INVENTION

The invasive electric stimulation device of the present invention includes a cathode and anode, each comprising a thin electrically conductive sheet having one exposed surface and the opposite surface covered with an insulation layer. A pair of insulated leads connect the cathode and anode to an implantable power pac which includes a source of electric power and an insulating encasement surrounding the same. The cathode may be laminar in construction including a plurality of spaced-apart frequency modulation channel monitors embedded within an insulation layer adjacent the conductive sheet and further including a top insulation layer with a reinforcement grid molded therein for strengthening the cathode and for shaping it to conform to a selected body surface. The FM channel monitors are electrically connected to an FM telemetry component within the power pac for transmitting signals indicative of the electrical characteristics of deposited bone callus, cartilage and soft tissue and therefor, the healing response of a fracture to electrical stimulation. A frequency modulated current regulator may be added to the power pac for adjusting the amperage in response to FM control signals from a remote transmitter. Adjustment of the current flow may be automatically accomplished by providing an implantable computer assisted device responsive to external programming communicated to it by a remote FM transmitter.

DESCRIPTION OF THE PREFERRED EMBODIMENTS

Figure 1:
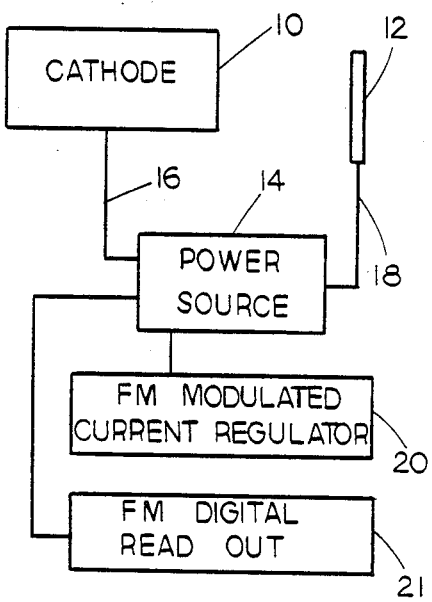
FIG. 1 is a block diagram of the electrical circuit of the invention.

FIG. 1 illustrates the basic elements of the invention in block form. The invasive electric stimulation device includes an implantable cathode 10, an implantable anode 12 and a power pac indicated generally at 14. These are interconnected by respective cathode and anode leads 16 and 18. The remotely controlled FM modulated current regulator 20 is electrically connected to the power source 14 as is an FM digital readout for remotely monitoring the healing process.

Figures 2, 2A:
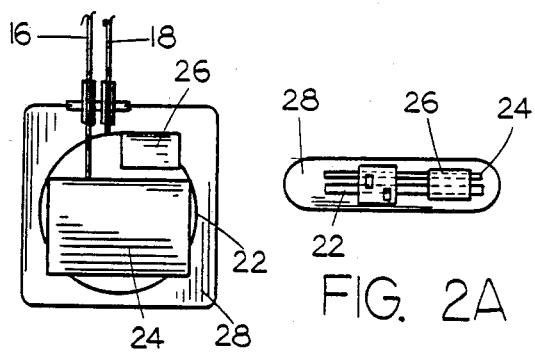
FIG. 2 is an enlarged cut-away top view of the power pac of the invention.
FIG. 2A is an enlarged cut-away end view of the power pac.

FIGS. 2 and 2A are an enlarged illustration of the power pac 14. A principal element is the battery 22 and the associated cathode and anode leads 16 and 18. The power pac also includes a silicon chip 24 of the current regulator 20, an FM telemetry component 26 and the encasement 28.

The FM telemetry component 26 may be of the general type manufactured by Biotelemetrics, Inc. of Westlake, Ohio, specifically their implantable FM radio transmitters, Models CFM-6 and CFM-8 and their electronic switching chip, Model SWP-1 which greatly extends the longevity of an implant requiring periodic measurements over a long term.

Figure 3:
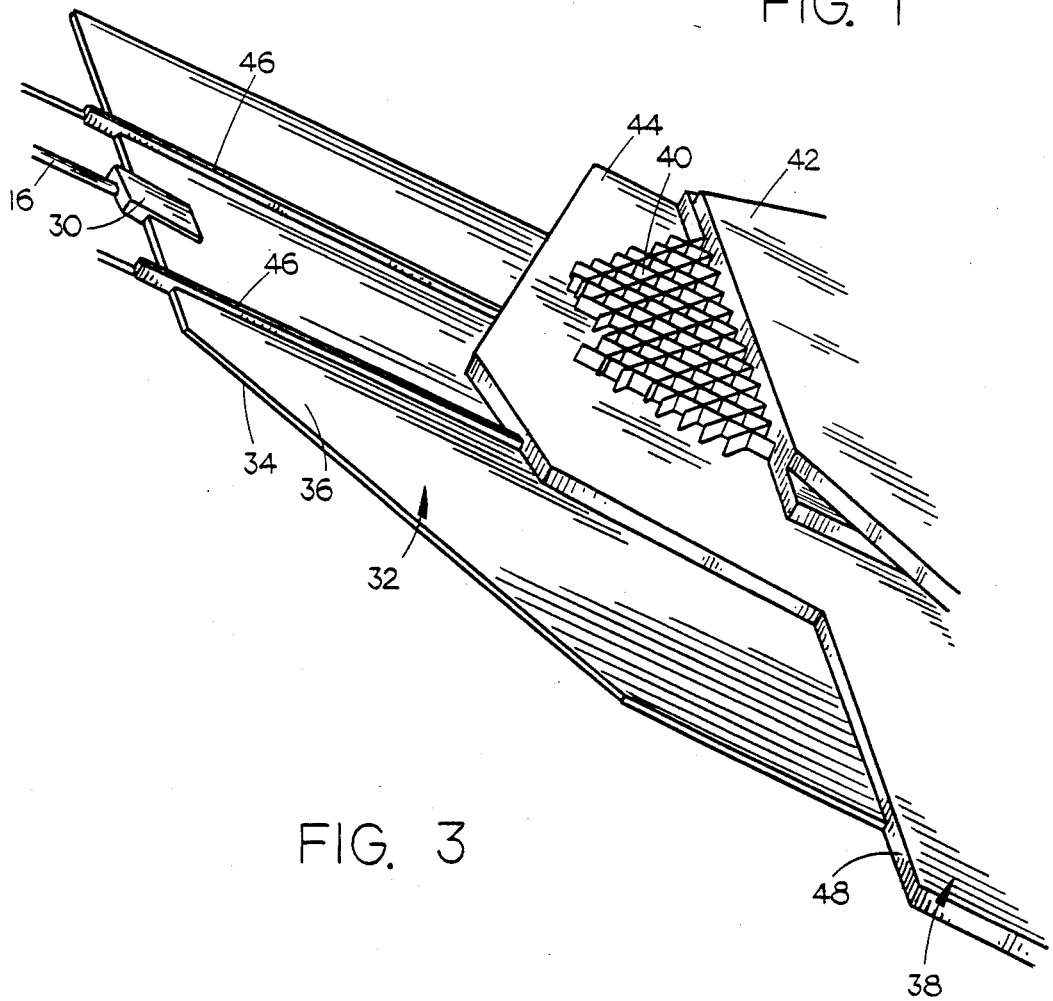
FIG. 3 is an enlarged perspective view of the cathode with portions cut away for clarity.

A preferred cathode structure is illustrated in FIG. 3 wherein the cathode lead 16 is electrically connected by a terminal 30 to a thin electrically conductive sheet 32 having an exposed surface 34 and an opposite surface 36 secured to and covered by an insulation layer 38 to protect against the dissipation of charge from surface 36. The insulation layer is preferably of laminar construction including a nylon mesh reinforcement 40 sandwiched between a pair of silicon layers 42 and 44. A plurality of channel monitors 46 are embedded within the cathode 10 in contact with the sheet 32 for monitoring resistance at different positions on the cathode.

The thin laminar construction of the cathode facilitates placement in areas where bulk mass could not be implanted. The thin sheet-like structure also enables easy implantation between tissue planes without interruption of important soft tissue vascularity for attachment about fractures. The sheet-like structure increases the tissue or bone surface area covered, decreases charging accumulation and tissue necrosis, increases cellular response and vascularity in a larger surface area of the reactive or fragmented vascularised periosteum and soft tissue. This structure also permits a closer proximity between the cathode and anode and treatment of complex fractures.

The cathode sheets can be prepared in various sizes and shapes so as to properly apply the field of electrical stimulation to incorporate the roll of the defect to be covered in fracture and grafting, to incorporate important soft tissue vascularity in the field and to allow for contour change. The cathode size will vary for pediatric and adult patients and will also vary depending upon the location of the defect, injury and graft bed to accommodate cranial, facial and irregular small and large bones and connective tissue supportive structures. It is always an object to maximize the field area of the fracture or graft to maintain viability of the parenchymal tissue, promote vascularity, minimize time required for the graft to "take" or the fracture to respond and to minimize external evidence of the device and physical disruption to the graft, bone or soft tissue.

The efficient insulation layer 38 protects the surrounding soft tissue and assures current dissipation in one plane. This is important for fracture field orientation and to prevent "leeching" of important current density, current charge and erroneous (F.E.T.) field effect transistor readings of change and resistance because of lack of insulation.

It is seen that the insulation layer 38 of the cathode 10 extends beyond conductive sheet 32 to provide a border 48.

"Stay-sutures" in the form of slotted holes may be provided along border 48 for maintaining the position of the cathode. Another option is to incorporate small bendable ribs in the insulation layer to facilitate trading the desired contour for the cathode.

It is important that the cathode lead 16 extending from the silicon chip 24 to the cathode 10 be electrically insulated to protect the surrounding tissue.

Figure 4:
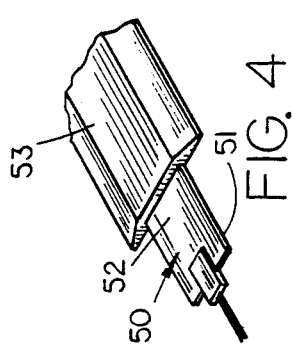
FIG. 4 is an enlarged perspective view of the anode with portions broken away for clarity.

FIG. 4 is an enlarged cut-away view of the anode 12 of the invention, including an electrically conductive strip or sheet 50 having an exposed under surface 51 and an opposite surface 52 which is connected to and covered by an insulation layer 53. As in the cathode shown in FIG. 3, the insulation is shown cut away for clarity but actually extends over the entire upper surface 52 of the anode. The anode 12 likewise may be provided in various sizes as dictated by the needs of producing optimal healing response in fractures or bone or soft tissue grafting procedures. Thicknesses of approximately 1/10 inch for the cathode and 1/16th inch for the anode are preferred but not critical.

Likewise, the number of anodes may be varied to maximize the area for current dissipation, to minimize tissue necrosis from excessive anodal charge and to allow closer proximity to the cathode. The combination of these objectives has not heretofore been achieved or addressed by any other invasive or noninvasive device.

Whereas each individual anode is generally smaller than the cathode with which it is used, it is similarly constructed to provide charge dissipation in a plane and to protect the surrounding soft tissue.

Figure 5:
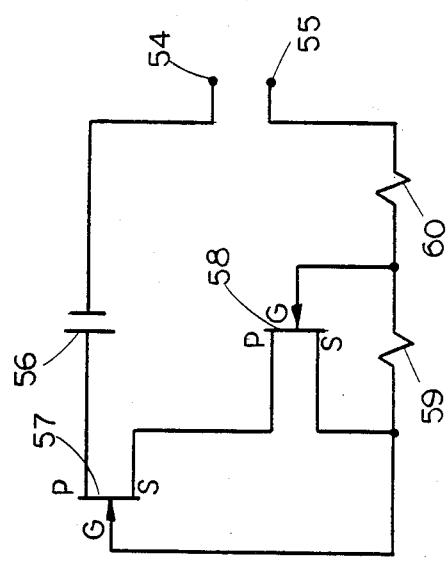
FIG. 5 is an electrical schematic diagram of a current control circuit for the invention.

Referring to FIG. 5, an electrical circuit is shown for an invasive electrical stimulation device. Terminal 54 provides for connection to the cathode 10 and terminal 55 provides for connection to one or more anodes 12. The current source 56 may be provided as a 7 volt battery, for example. The circuit further includes a pair of transistors 57 and 58 which may be field effect transistors of the type referred to as MPF103, and a pair of resistors 59 and 60 having respective resistances of 150 Kohms and 100 Kohms respectively. Manipulation of the circuit at various points results in increased or decreased microamps of current. Furthermore, the circuit may provide for a readout of current density at the cathode, and a measure of the change between the cathode, anode, tissue, etc.

Figure 6:
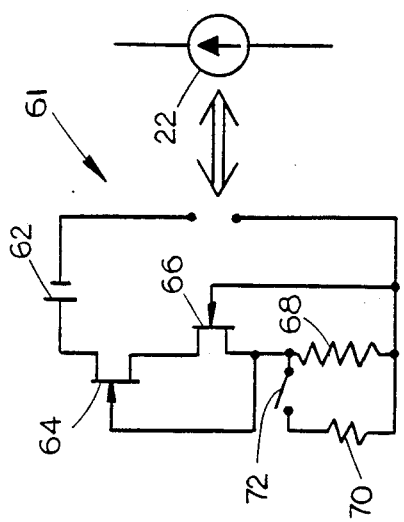
FIG. 6 is an electrical circuit diagram including a current control switch.

With reference to FIG. 6, another current control circuit is shown. Circuit 61 includes a battery 62 electrically connected through a pair of transistors 64 and 66 to a large resistor 68. A smaller resistor 70 is connected in parallel with large resistor 68 with a switch 72 interposed therebetween. Switch 72 allows two states of current. With the switch closed, approximately twice the current would flow.

Figure 7:
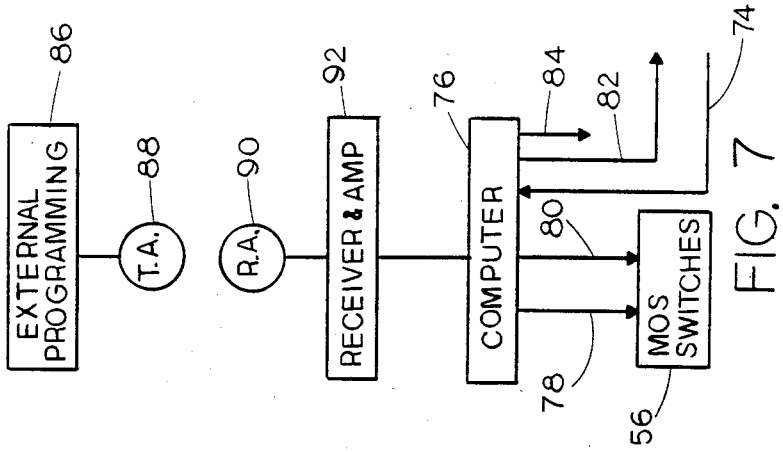
FIG. 7 is a block diagram of an electrical circuit including automatic cathode monitoring and current adjustment.

A more sophisticated control circuit is shown in block diagram form in FIG. 7. A D/C voltage sampler would provide a digital signal on line 74 to a CMOS computer chip 76. The computer output would include signals on lines 78 and 80 for controlling the MOS switches 56; D/A signals could be sent out on line 82 to switch data to a transmitter for relaying data out and a D/A output on line 84 to be operative for current control. The computer chip 76 could be externally programmed as indicated at 86, which programming would be communicated from an external transmitter antenna 88 to an implanted receiver antenna 90 to a receiver and amp 92 for input to the computer chip 76. Thus, software could take over the complete control of the current switching and current amperage setting.

Figure 8:
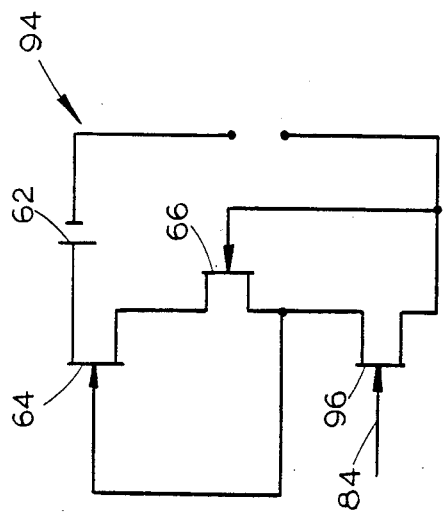
FIG. 8 is another electrical circuit diagram wherein the current source is controlled by the D/A convertor.

In this application, a modified current source such as the circuit 94 of FIG. 8 would be substituted for the circuit 61 of FIG. 6. With the current control signals communicated to a transistor 96, the current source would be controlled by the D/A convertor.

It is anticipated that the circuits of FIGS. 5, 6 and 8 would be embodied in the form of silicon chips to use solid state, to reduce size and to reduce wear and possible errors of manufacture. Such chips are custom-made on a contract basis by various manufacturers.

The computer 76 could be programmed to be an adaptive filter which would adapt to an environment which is modeled as a set of parameters to be measured.

Figure 9A:
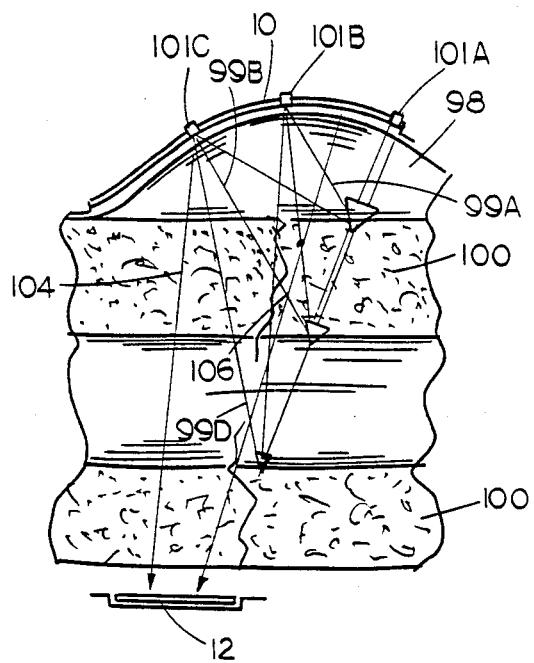
FIG. 9A is a partial diagrammatic sectional view of a fracture undergoing electrical stimulation.
Figure 9B:
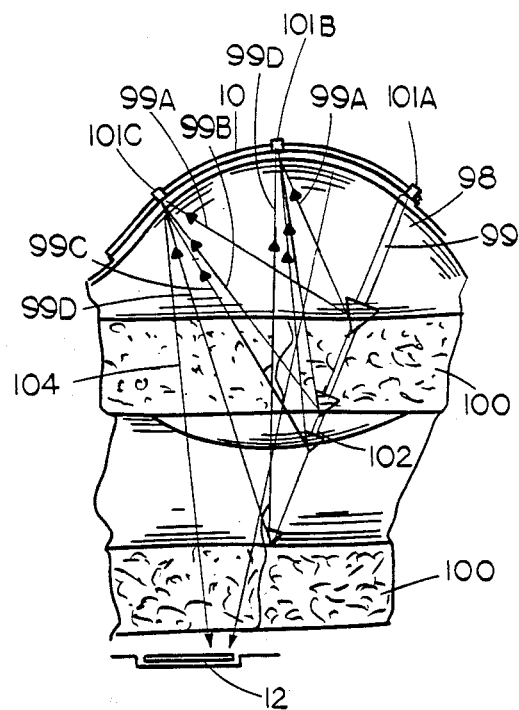
FIG. 9B is a view similar to FIG. 9A but showing advanced healing adjacent the fracture.

FIG. 9A is a cross sectional view of a fracture after approximately three weeks of electrical stimulation. A periosteum buildup 98 is formed on the bone 100 adjacent the cathode 10. FIG. 9B illustrates the same fracture after approximately four weeks of electrical stimulation. It is seen that the periosteum buildup 98 has increased in volume and that the buildup has extended to the interior of the bone as indicated at 102. The insulation on the exterior surfaces of both the anode and cathode effectively block soft tissue diffusion of current through the soft tissue around the bone. Thus all of the dissipated current is utilized to full advantage.

Healing progress is monitored with a signal 99 generated from a point 101A on the cathode. The process involves a phenomena similar to that employed in seismic geological study of impulse response in strata of ground, as described in Ender's A. Robbinson's texts entitled (1) "Signal Response" and (2) "Multichannel Time Series Analysis with Digital Computer Programs." Signal 99 traverses various thicknesses and layers of different healing callus 98, bone 100, soft tissue and cartilage. The signal travels through different medium at different speeds and reflects inverse impulse responses 99A, B, C and D at the various boundary surfaces between layers. Receivers at points 101B and 101C record the changes in the intensity of the impulse responses over time. These recordings are then studied at rapid speed by computer to determine which impulse responses correspond to bone, soft tissue and cartilage. These parameters are recorded to study from past "readouts". Thus, measurement of the reflected impulse responses is used to quantify the healing callus.

Figure 10A:
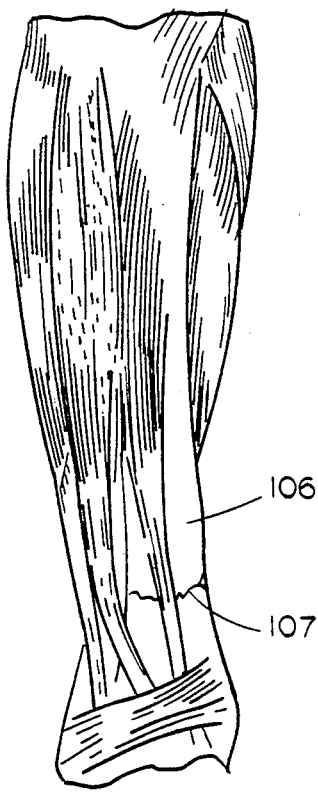
FIG. 10A is a partial elevational view of the interior of a leg with a fractured tibia.
Figure 10B:
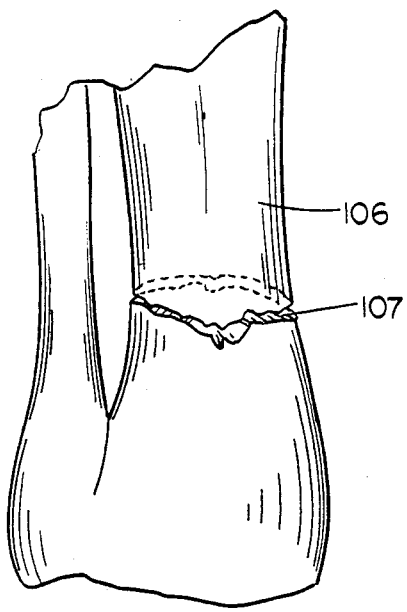
FIG. 10B is an enlarged, detail perspective view of the fracture area of the tibia.
Figure 10C:
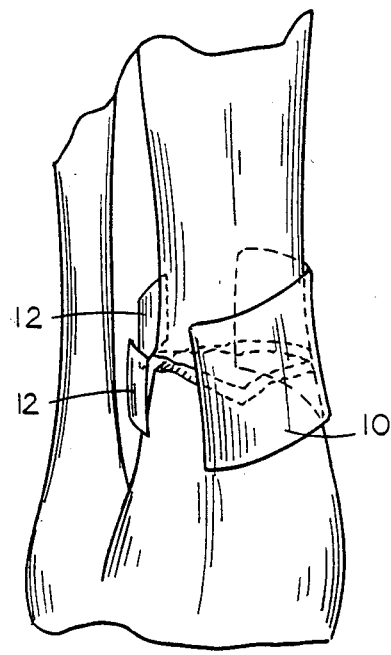
FIG. 10C is an enlarged perspective view of the fractured tibia with the anode and cathode sheets of the invention applied thereto.

FIGS. 10A-10C illustrate a procedure wherein a simple fracture is stimulated invasively without grafting. FIG. 10A illustrates a tibia 106 having a fracture indicated at 107. The same fracture is shown in enlarged form in FIG. 10B. FIG. 10C illustrates the invasive placement of the cathode 10 and a pair of anodes 12 for electrically stimulating the fracture.

Figure 10D:
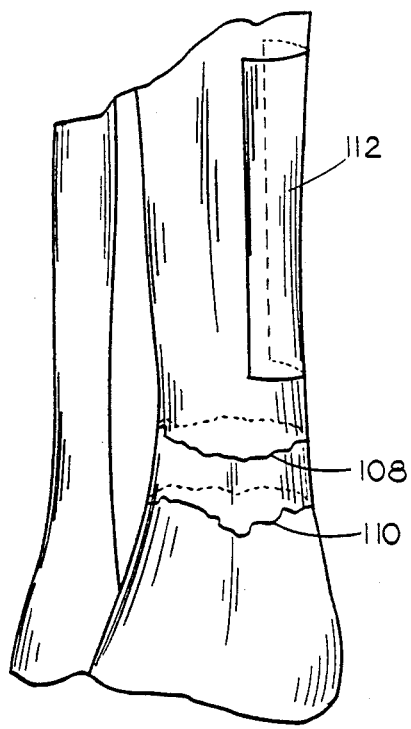
FIG. 10D illustrates the periosteum bed for treatment of a long bone fracture.
Figure 10E:
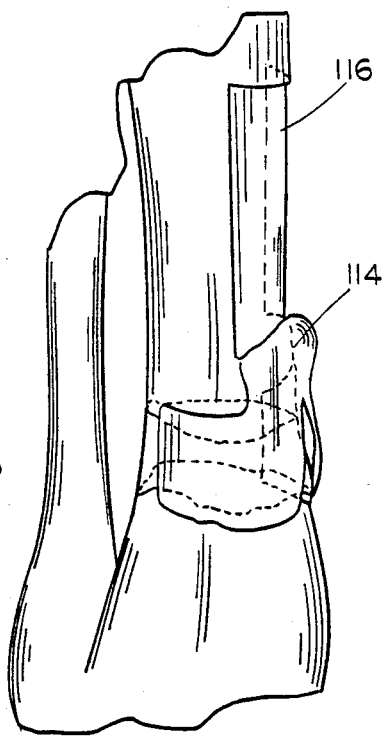
FIG. 10E is a perspective view showing the periosteum pedicule graft in place over the fracture.
Figure 10F:
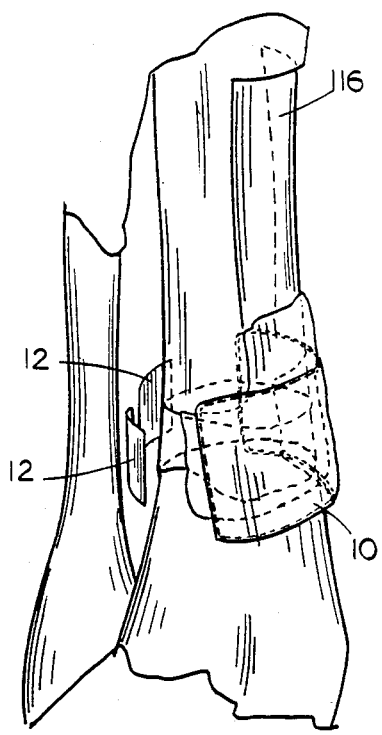
FIG. 10F is a partial perspective view showing the anode and cathode of the invention applied over the periosteum pedicule graft on the tibia.

FIGS. 10D-10F illustrate the treatment of a fracture with a greater degree of bone nonunion, as indicated by fracture lines 108 and 110. FIG. 10D illustrates the periosteum bed or flap 112 from which the periosteum pedicule graft 114 in FIG. 10E is taken. The "primed" periosteo flap 114 is used to carry osteogenic potential growth over the defect. "New bone" or osteoid will grow on and into the defect while replacing the deficit from the graft also. Accordingly, there is periosteum regrowth at 116 also. FIG. 10F shows the placement of the cathode 10 and anodes 12 without trauma to the callus and with the incorporation of second degree soft tissue from various approaches.

Figure 11C:
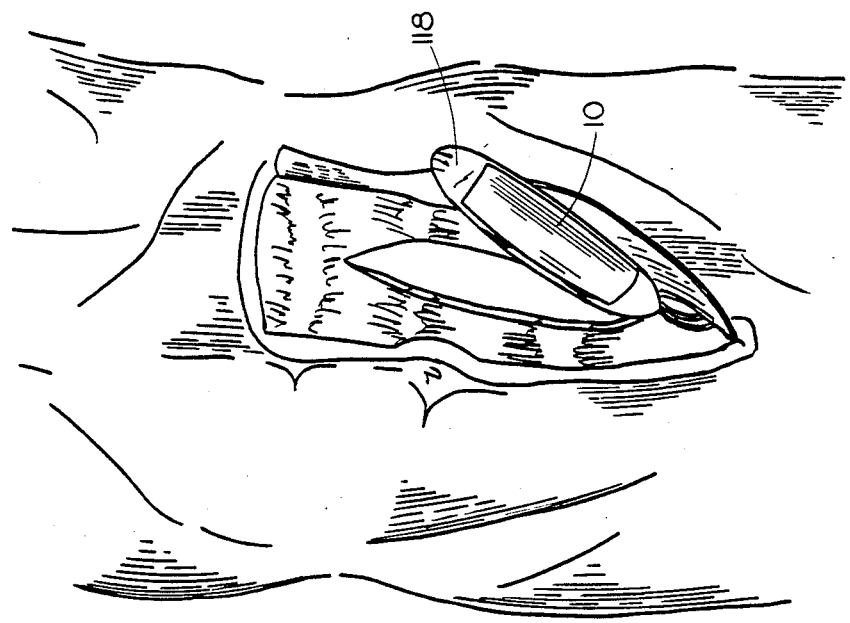
FIG. 11C illustrates the osteoid harvested on the vascular pedicule with muscle flap as the vascular source.
Figure 11B:
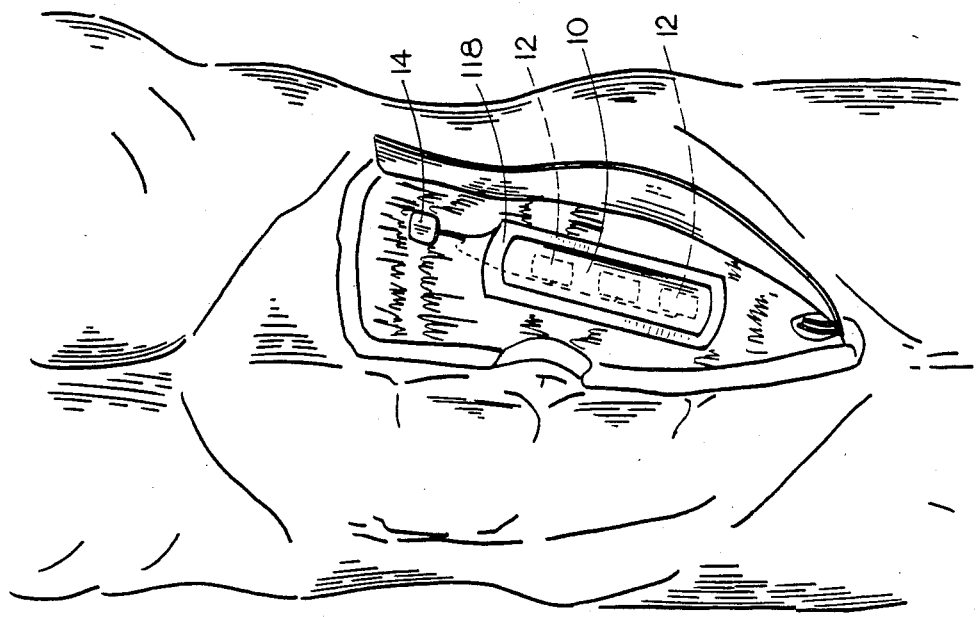
FIG. 11B illustrates continued electrical stimulation of the periosteum in a graft bed.
Figure 11A:
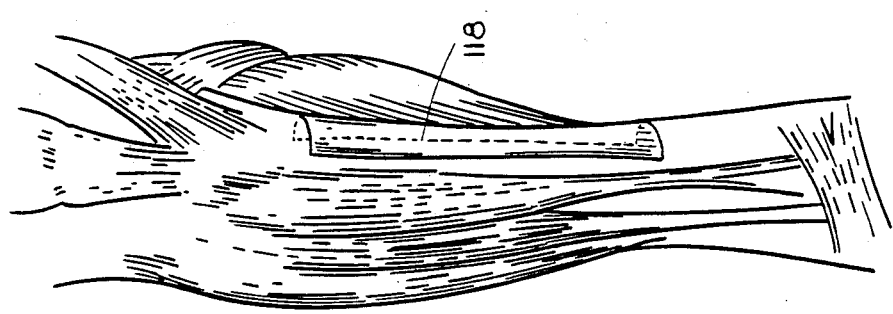
FIG. 11A is a side elevational view of a tibia showing the "primed" periosteum.

FIGS. 11A-C and FIGS. 12A-B illustrate a procedure using a free graft of periosteum. In FIG. 11A, there is shown a "primed" or previously electrically stimulated periosteum 118 which is execised for ingrowth to the vascular bed. Priming the periosteum with electrical stimulation engages the cells to increase in number and function, preferably for five to seven days, and to create an exuberant callus. FIG. 1B shows the periosteum graft matured on vascular ingrowth potential (muscle) with the implanted cathode 10, anode 12 and power pac 14 shown in place. Electrical stimulation is continued to ensure cell viability, vascular ingrowth and osetoid production (bone) in the graft bed.

Finally, in FIG. 11C, the vascularized new bone/periosteum is harvested on the arterial venous pedicule with the muscle flap as the vascular source.

Figure 12A:
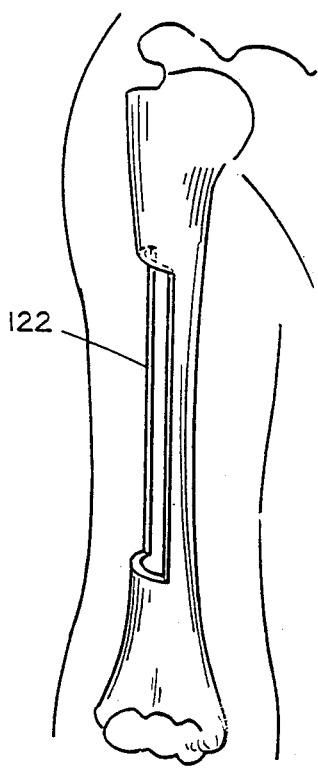
FIG. 12A is a diagrammatic illustration of a humerus having a prepared defect.
Figure 12B:
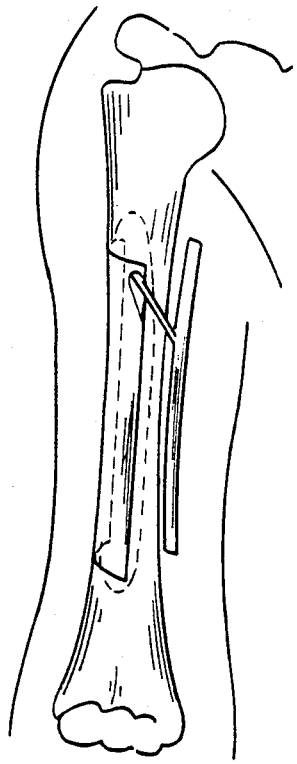
FIG. 12B is a diagrammatic illustration of the humerus having the free graft with vascular anastomsis to fill the bone defect.

With reference to FIG. 12A, the next step is to prepare the donar field to be ready for the incorporation of "new bone". The donor bed 122 is cleaned to viable bone, for example by removal of tumor or dead tissue from secondary trauma. The viable graft 118 is anastomosed (artery and vein) and continually electrically stimulated to heal the graft margins, maintain the cells of the graft and promote vascularity into the graft until completely healed. This procedure is useful for treatment of gross defects from second degree tumor loss, trauma, infection, and congenital defects with structural weakness.

Thus there has been shown and described an improved apparatus and method for invasive electrical stimulation of bone fractures which accomplishes at least all of the stated objects.

I claim:

1. An invasive electric stimulation device, comprising,
   a cathode comprising a thin electrically conductive sheet having
   an exposed surface and an opposite surface, an insulation layer connected to said conductive sheet and covering said opposite surface to protect against the dissipation of charge therefrom,
   a plurality of elongated spaced-apart channel monitors electrically connected to and extended across said cathode conductive sheet toring the resistance between said cathode and an anode,
   said anode comprising a thin electrically conductive sheet having an exposed surface and an opposite surface, an insulation layer connected to said conductive sheet of the anode and covering said opposite surface thereof,
   an implantable power pac including a source of electric power having positive and negative terminals, and an insulating encasement surrounding said source of electric power,
   an insulated cathode lead electrically connected to and extended between said negative terminal of said source of electric power and said conductive sheet of the cathode, and
   an insulated anode lead electrically connected to and extended between said positive terminal of said source of electric power and said conductive sheet of the anode.

2. The device of claim 1 wherein said insulation layer of the cathode has a reinforcing grid included therein.

3. The device of claim 2 wherein said insulation layer is formed of silicon and said reinforcing grid comprises a nylon grid molded into the silicon insulation.

4. The device of claim 1 wherein said insulation layer includes a border extending beyond the edges of the cathode conductive sheet.

5. The device of claim 4 wherein said border includes a plurality of suture rip-out ports.

6. The device of claim 1 wherein said power pac further comprises an FM telemetry component, including a radio transmitter and electronic switching chip, electrically connected to the channel monitors of said cathode and to said source of electric power, said FM telemetry component being operative to transmit a signal indicative of the monitored resistance on a selected channel of said channel monitors.

7. The device of claim 6 wherein said power pac further comprises a frequency modulated current regulator, including an FM receiver and antenna, electrically interposed between said source of electric power and cathode and operative to adjust current flow from said source of electric power in response to receipt of FM control signals from a remote transmitter.

8. An invasive electric stimulation device, comprising,
   a cathode comprising a thin electrically conductive sheet having an exposed surface and an opposite surface, an insulation layer connected to said conductive sheet and covering said opposite surface to protect against the dissipation of charge therefrom,
   an anode comprising a thin electrically conductive sheet having an exposed surface and an opposite surface, an insulation layer connected to said conductive sheet of the anode and covering said opposite surface thereof,
   an implantable power pac including a source of electric power having positive and negative terminals, and an insulating encasement surrounding said source of electric power,
   an insulated cathode lead electrically connected to and extended between said negative terminal of said source of electric power and said conductive sheet of the cathode,
   an insulated anode lead electrically connected to and extended between said positive terminal of said source of electric power and said conductive sheet of the anode,
   a current regualtor electrically associated with said source of electric power,
   monitoring means electrically associated with said cathode, anode, power source and current regulator, for measuring electrical resistance between said cathode and anode as a measure of the thickness of the various layers of periosteum buildup, bone, soft tissue and cartilage in proximity of a fracture in response to electrical stimulation,
   and a computer assisted device associated with said power pac and monitoring means and operative to automatically cause said current regulator to adjust current flow from said source of electric power in response to predetermined measurements of electrical resistance by said monitoring means.

9. A method of invasive electrical stimulation of a bone fracture to promote the healing thereof, comprising,
   providing a thin cathode having an exposed conductive sheet on one surface and an insulating layer on the opposite surface thereof, a thin anode comprising a conductive sheet covered on one surface by an insulation layer, a power pac including a source of electric power, and means for monitoring the electrical resistance between said cathode and anode, said monitoring means adapted for remote monitoring,
   surgically implanting said cathode and anode on diametrically opposing sides of a bone having a fracture with the conductive faces of said cathode and anode sheets overlapping the fracture,
   implanting said power pac and electrically connecting said power pac to the implanted anode and cathode, and
   remotely monitoring the thickness of the various layers of periosteum buildup, bone, soft tissue and cartilage in proximity to said bone fracture in response to electrical stimulation.

10. The method of claim 9 wherein said remotely monitoring step includes monitoring the thickness of said various layers at a plurality of spaced-apart positions on said cathode.

11. The method of claim 9 further comprising the steps of
   providing a computer assisted device electrically associated with said power pac and monitoring means,
   and said computer assisted device automatically increasing or decreasing the current flow across said cathode and anode in response to pre-programmed commands responsive to predetermined measurements monitored by said monitoring means.

* * * * *